United States Patent
Labreche et al.

(10) Patent No.: US 6,496,813 B1
(45) Date of Patent: Dec. 17, 2002

(54) CLASSIFYING APPARATUS USING A COMBINATION OF STATISTICAL METHODS AND NEURONAL NETWORKS, DESIGNED IN PARTICULAR FOR ODOUR RECOGNITION

(75) Inventors: Saïd Labreche, Toulouse (FR); Hicham Amine, Balma (FR); Tze Tsung Tan, Toulouse (FR); François Loubet, Balma (FR)

(73) Assignee: Alpha M.O.S., Toulouse (FR)

( * ) Notice: Subject to any disclaimer, the term of this patent is extended or adjusted under 35 U.S.C. 154(b) by 0 days.

(21) Appl. No.: 09/486,780
(22) PCT Filed: Sep. 4, 1998
(86) PCT No.: PCT/FR98/01897
§ 371 (c)(1), (2), (4) Date: May 1, 2000
(87) PCT Pub. No.: WO99/12029
PCT Pub. Date: Mar. 11, 1999

(30) Foreign Application Priority Data

Sep. 4, 1997 (FR) ............................................. 97 11001

(51) Int. Cl.$^7$ ............................................. G06F 15/18
(52) U.S. Cl. ............................. 706/20; 702/22; 702/27; 700/48
(58) Field of Search ....................... 706/20; 702/22–33; 700/48

(56) References Cited

U.S. PATENT DOCUMENTS

| | | | | |
|---|---|---|---|---|
| 5,177,994 A | * | 1/1993 | Moriizumi et al. | 73/23.34 |
| 5,373,452 A | * | 12/1994 | Guha | 702/33 |
| 5,526,281 A | * | 6/1996 | Chapman et al. | 702/22 |
| 6,081,766 A | * | 6/2000 | Chapman et al. | 702/27 |

FOREIGN PATENT DOCUMENTS

| | | |
|---|---|---|
| EP | 0 632 268 | 1/1995 |
| EP | 0 733 880 | 9/1996 |

OTHER PUBLICATIONS

Odor sensor using quartz–resonator array and neural–network pattern recognition, Nakamoto, T.; Moriizumi, T.; Ultrasonics Symposium, 1988. Proceedings., IEEE 1988, 1988, pp. 613–616 vol. 1.*

Neurodynamic approach to odor processing, Erdi, P.; Barna, G.; Neural Networks, 1991., IJCNN–91–Seattle International Joint Conference on, vol.: ii, 1991, pp.: 653–656.*

Perfume and flavor identification by odor sensing system using quartz–resonator sensor array and neural–network pattern recognition, Nakamoto, T.; Fukuda, A.; Moriizumi, T.; Solid–State Sensors and Actuators, 1991. Digest of Technical Papers, 1991 IEEE.*

(List continued on next page.)

Primary Examiner—Thomas Black
Assistant Examiner—Michael B. Holmes
(74) Attorney, Agent, or Firm—Weingarten, Schurgin, Gagnebin & Lebovici LLP

(57) ABSTRACT

The invention concerns a classifying apparatus, used in particular for recognising or characterising odours, applying a combination of statistical methods and neuronal networks to classify into the appropriate class instances of a plurality of different classes presented to the apparatus. The apparatus comprises a processing unit for determining for each class (j) a subspace (SEj) wherein the instances of said class are best separated from instances of other classes, said subspace being defined by synthetic variables (VDj), and for determining a discriminating subspace (SED) defined by the whole set of synthetic variables identified for the whole set of classes. Each neuron in the neuronal input layer corresponds to one of the variables defining the discriminating space (SED) and each neuron of the output layer corresponds to one of the classes.

18 Claims, 4 Drawing Sheets

OTHER PUBLICATIONS

Artificial neural networks and statistical pattern recognition improve MOSFET gas sensor array calibration, Sundgren, H.; Winquist, F.; Lundstrom, I. Solid–State Sensors and Actuators, 1991. Digest of Technical Papers, pp.: 574–577.*

Odor sensing system using neural network pattern recognition, Moriizumi, T.; Nakamoto, T.; Industrial Electronics, Control, Instrumentation, and Automation, 1992. Power Electronics and Motion Control, pp.: 1645–1649 vol. 3.*

Temporal Pattern Classification in The Model Of Olfactory Cortex, Yamafuji, T.; Kashimori, Y.; Kambara, T.; Neural Networks, 1993. IJCNN '93–Nagoya. Proceedings of 1993 International Joint Conference on, vol.: 1, pp.: 85–88.*

Feature extraction from mixed odor stimuli based on spatio–temporal representation of odors in olfactory bulb, Hoshino, O.; Kashimori, Y.; Kambara, T.; Neural Networks, 1997., International Conference on, vol.: 1, 1997, pp.: 344–349.*

Heirarchical classification of odor quality based on dynamical property of neural network of olfactory cortex, Oyamada, T.; Kashimori, Y.; Kambara, T.; Neural Networks, 1997., International Conference on, vol.: 1, 1997 pp.: 586–590.*

Feature–level signal processing for odor sensor arrays, Roppel, T.; Dunman, K.; Padgett, M.; Wilson, D.; Lindblad, T. Industrial Electronics, Control and Instrumentation, 1997. IECON 97. 23rd International, Conference on, vol.: 1, 1997.*

Reinforcement learning neural network circuits for electronic nose, Abdel–Aty–Zohdy, H.S.; Al–Nsour, M.; Circuits and Systems, 1999. ISCAS '99. Proceedings of the 1999 IEEE International, Symposium on, vol.: 5, 1999, pp.: 379–382, vol. 5.*

Digital neural processing unit for electronic nose, Abdel–Aty–Zohdy, H.S.; Al–Nsour, M.; VLSI, 1999. Proceedings. Ninth Great Lakes Symposium on, 1999 pp.: 236–237.*

Improvement of artificial odor discrimination system using fuzzy–LVQ neural network, Kusumoputro, B.; Widyanto, M.R.; Fanany, M.I.; Budiarto, H.; Computational Intelligence and Multimedia Applications, 1999. ICCIMA '99, Proceedings, pp.: 474–478.*

Nonlinear cluster transformations for increasing pattern separability, Polikar, R.; Udpa, S.S.; Neural Networks, 1999. IJCNN '99. International Joint Conference on, vol.: 6, 1999, pp.: 4006 –4011 vol. 6.*

Odor detection using pulse couple neural networks, Szekely, G.; Padgett, M.L.; Dozier, G.; Roppel, T.A.; Neural Networks, 1999. IJCNN '99. International Joint Conference on, vol.: 1, 1999, pp.: 317–321 vol. 1.*

Overview of electronic nose algorithms, Keller, P.E.; Neural Networks, 1999. IJCNN '99. International Joint Conference on, vol.: 1, 1999, pp.: 309 –312 vol. 1.*

A new linguistic fuzzy approach to recognition of olfactory signals, Lazzerini, B.; Maggiore, A.; Marcelloni, F.; Neural Networks, 1999. IJCNN '99. International Joint Conference on, vol.: 5, 1999, pp.: 3225 –3229 vol. 5.*

Study of digital learning circuit for odor sensing system using 1–bit data stream signal processing circuit, Nakamoto, T.; Kawamura, S.; Moriizumi, T.; Neural Networks, 1999. IJCNN '99. International Joint Conference on, vol.: 4, pp. 2425–2428 vol. 4.*

Using neural networks and genetic algorithms to enhance performance in an electronic nose, Kermani, B.G.; Schiffman, S.S.; Nagle, H.T.; Biomedical Engineering, IEEE Transactions on, vol.: 46, Issue: 4, Apr. 1999 pp.: 429–439.*

A nose gesture interface device: extending virtual realities, Tyson R. Henry; Scott E. Hudson; Andrey K. Yeatts; Brad A. Myers; Steven Feiner; ACM Special Interest Group on Computer Graphics and Interactive Techniques, ACM Press 1991 pp.: 65–68.*

Corcoran P., Electronic Odour Sensing Systems Electronics and Communication Engineering Journal, vol. 5, No. 5, Oct. 1, 1993, pp 303–308**.

Chastrette M et al., "Tetralin, indan and nitrobenzene compound structure–musk odor relationship using neural networks" European Journal of Medicinal Chemistry. Chimica Therapeutica, vol. 30, No. 9, 1995, p. 679–686**.

* cited by examiner

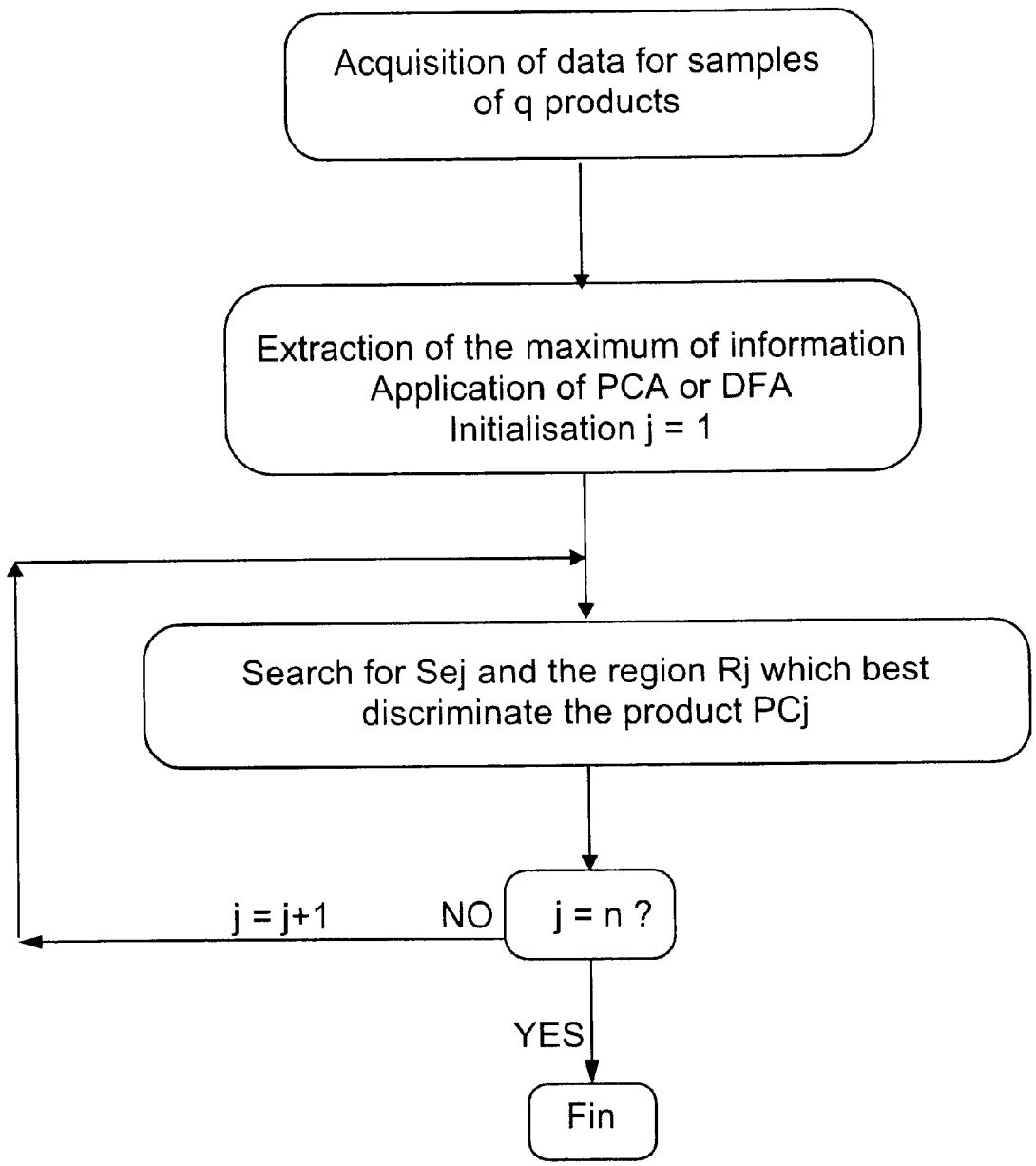
Figure 1 : Search for specific regions

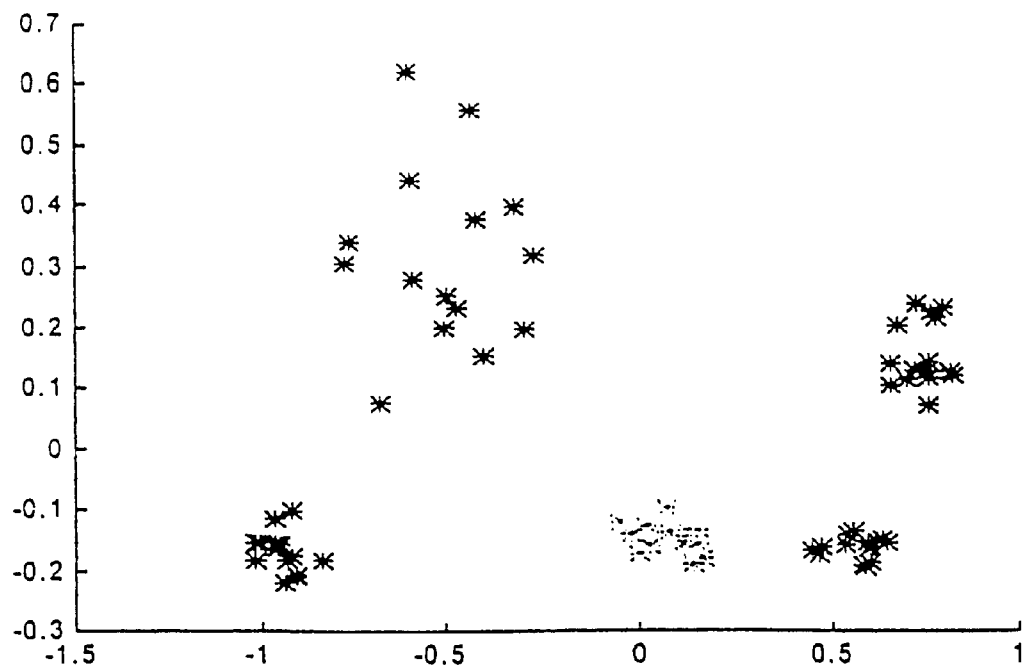
Figure 2A : Discriminating Plane
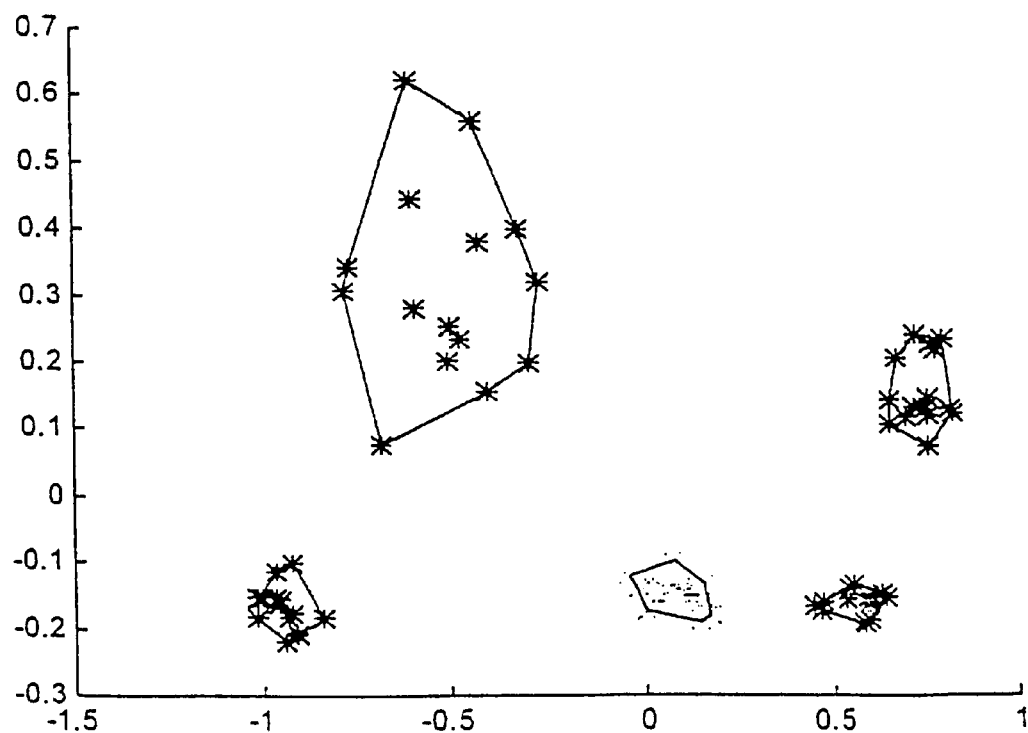
Figure 2B : convex envelopes delimiting the different regions

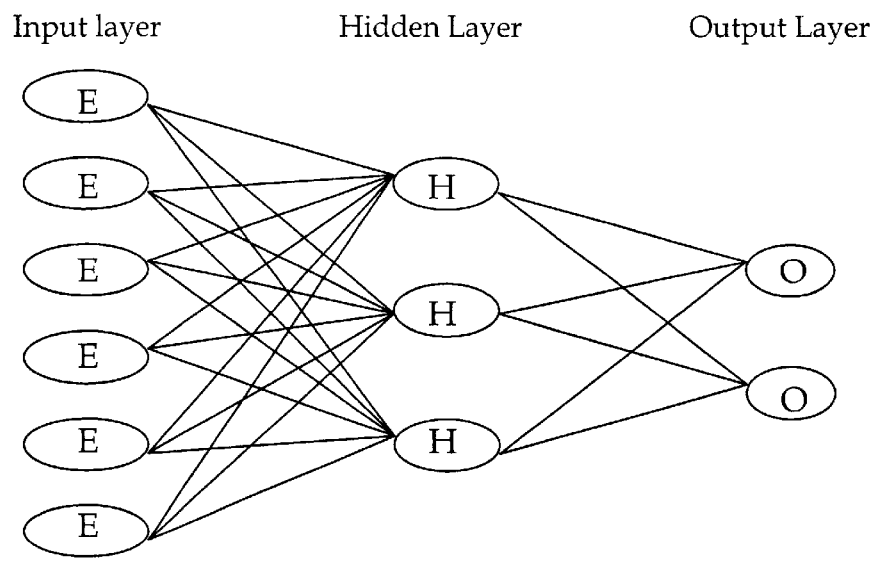
Figure 3 : Neural Network
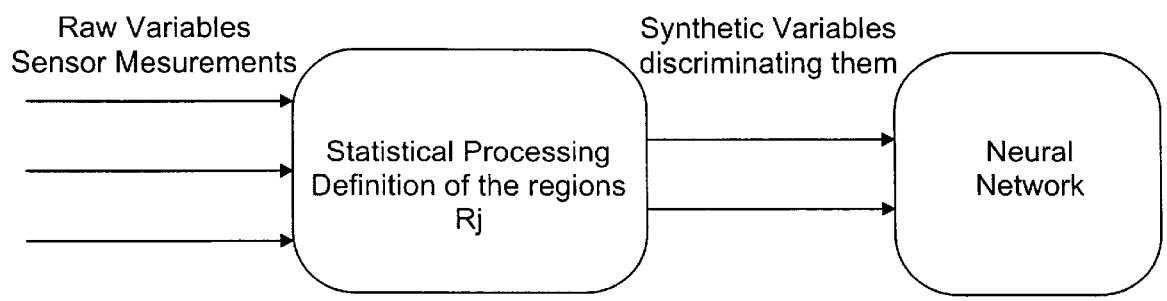
Figure 4 : Diagram of construction of the neural network

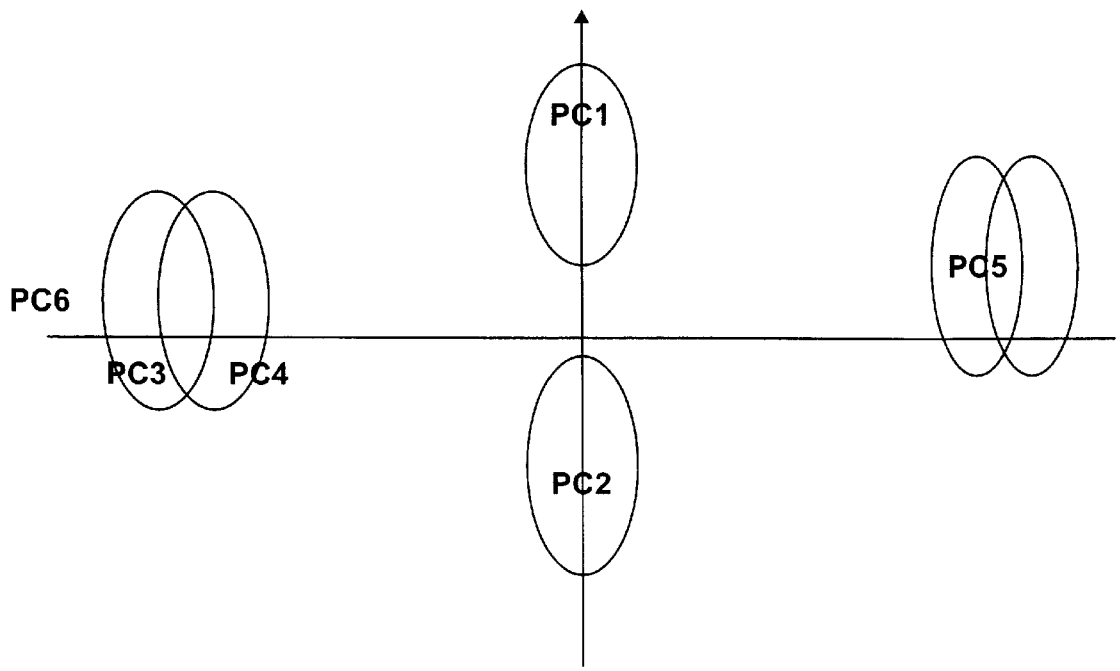
Figure 5 : Example of Sub-space Sej
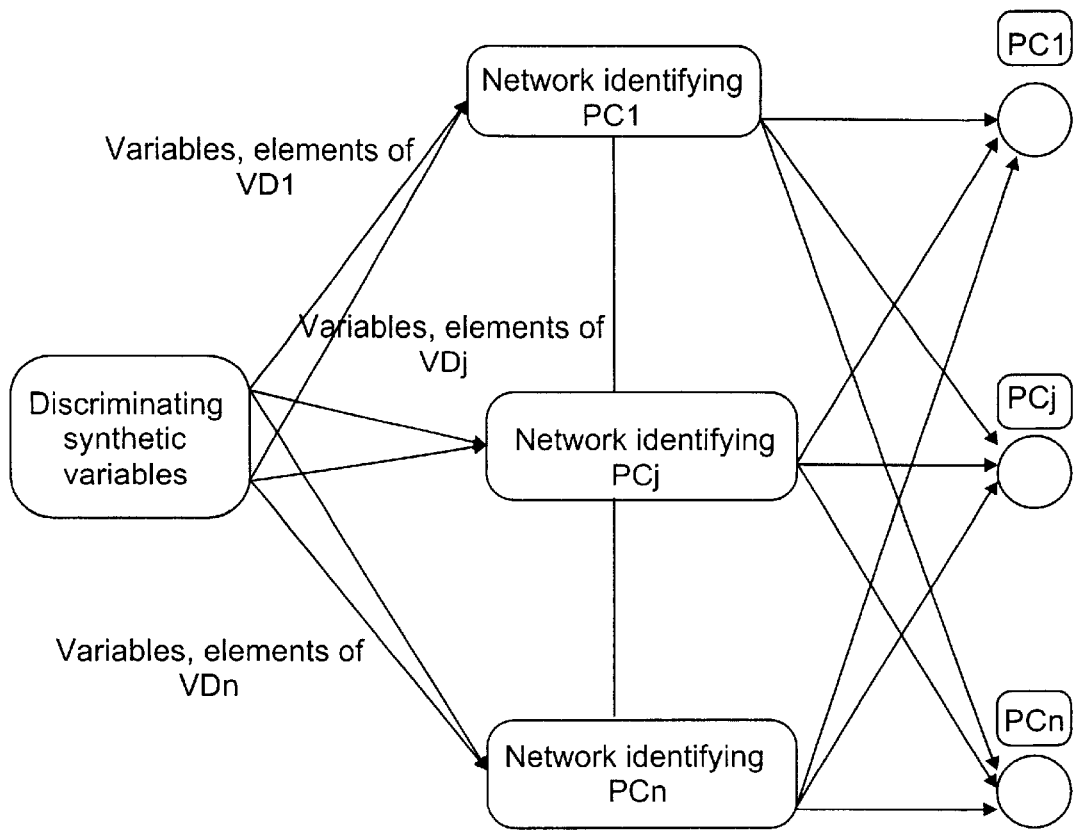
Figure 6 : Example of the combinational network

CLASSIFYING APPARATUS USING A COMBINATION OF STATISTICAL METHODS AND NEURONAL NETWORKS, DESIGNED IN PARTICULAR FOR ODOUR RECOGNITION

FIELD OF THE INVENTION

The present invention concerns pattern classification, notably in the field of the characterisation or the identification of odours.

BACKGROUND OF THE INVENTION

In odour characterisation or identification apparatus (so-called "electronic noses") a sample of an unknown product is identified by classifying it in one of several classes which the apparatus recognises thanks to a preliminary learning operation. Apparatus of this type comprises two main parts, a data acquisition portion and a data processing portion. In general, the data acquisition portion comprises a sampling head enabling the sampling of volatile components which are given off by the tested product, and a battery of sensors to which the sampled components are supplied and which produce output signals which, taken together, are characteristic of the volatile components given off by the product and, thus, are characteristic of the product. In general, the data processing portion comprises automatic data processing means which record the sensors' output signals and perform analyses thereon. By detecting or analysing the patterns inherent in the different sets of data relating to particular products, the data processing portion detects the class of the product (which can correspond to the nature of the product, for example, "a wine", "a whisky", etc., or to a quality of a product, for example, "fresh milk", "fermented milk", etc.).

The goals pursued in acquiring and in processing the data are different depending upon whether the apparatus is in learning mode or in identification mode.

In the learning mode of the apparatus, the products from which the various samples are taken are known and are analysed several times. The processing methods which are used at this time are those which enable, on the one hand, the detection and characterisation of the different products and, on the other hand, the construction of a robust identification model. The methods used are generally statistical methods (Principal Component Analysis (PCA), Discriminant Factor Analysis (DFA), ... ) and neural networks (see, for example, J. W. Gardner and P. N. Bartlett, "Sensors and sensory systems for an Electronic Nose", Nato Asi, Series E, Vol. 212, pp.161–180 (1992)). In the identification phase, the origin of the samples is unknown and the goal is to identify this origin by using the data, and the model which has already been constructed.

The statistical methods used in processing the data recorded by an electronic nose are linear methods. The variables calculated according to such methods are so-called "synthetic variables" and convey two items of information, quantitative information, indicating the percentage of inertia in the initial cloud of points that is explained by this variable, and qualitative information regarding the structure and discrimination of the cloud which it discloses. By way of contrast, neural networks are among non-linear methods and are capable of learning the behaviour of the different sensors. The two types of methods directly employ the recorded raw data. In general, they are used separately.

Now, it is recalled that the expression "synthetic variables" refers to combinations (whether or not linear) of the measured variables. In general they are obtained by optimisation of a precisely defined criterion. The environment of this optimisation process can be conditioned by additional knowledge or variables. For example, in PCA a criterion is optimised without any additional information whereas, in DFA, there is available knowledge regarding each sample's affiliation to a group, and in PLS ("partial least square") one or several additional variables are measured for each sample (for example, the concentration of a particular chemical element).

The document WO96/26492 describes a particular neural network structure capable, amongst other things, of being used in electronic noses. This neural network comprises, in the output layer thereof, fuzzy logic neurones that enable it to be indicated that the tested product belongs to an unknown class. In this document, it is also proposed to increase the number of neurones in the input layer of the neural network so as to input not only the sensor output signals but also signals representing variables calculated in a Principal Component Analysis of the original signals, for example, the two or three first components of the PCA.

However, by adding wholesale, to the measured signals representing the data, signals resulting from a Principal Component Analysis of the data, in order to constitute the input signals to the neural network, WO96/26492 follows the approach of conventional techniques which superpose statistical methods and neural networks. Moreover, even though the variables obtained by a principal component analysis convey substantial quantitative information, their contribution in terms of qualitative information is not necessarily great, particularly when a large number of distinct products is being handled. Thus, the systematic use of a certain number of predetermined variables derived from a statistical analysis does not automatically ensure the discrimination of the different products. Furthermore, these variables are correlated with certain of the initial variables (channels) and, consequently, their use as input signals to the neural network leads to redundancy.

SUMMARY OF THE INVENTION

The present invention relates to a pattern classification apparatus notably for use in the field of odour recognition, in which the statistical methods and the neural techniques are intertwined so as to exploit to the greatest possible extent the synergy between them, and to a method for optimising such an apparatus during the learning phase thereof.

More particularly, the present invention provides a classification apparatus, notably for use in the recognition or the characterisation of odours, comprising: means for acquiring, during a learning phase and by a plurality of channels, raw data representing a plurality of instances of a plurality of different classes; a processing unit for processing said raw data so as to determine, for each class (j), characteristics common to different instances of the class; and a neural network for outputting a classification, into one of the classes, of an instance presented to said classification apparatus, said neural network comprising an input layer, an output layer and at least one intermediate layer disposed between the input and output layers, the output layer comprising a plurality of neurones each being adapted to recognise instances of a respective class from the plurality of classes: characterised in that the processing unit determines for each class (j) a sub-space (SEj) in which the instances of this class (j), for which raw data has been obtained, are optimally separated from the instances of all the other classes, said sub-space (SEj) being defined by a group (VDj)

of one or a plurality of synthetic variables (V), and determining the discrimination sub-space (SED) which comprises the sub-spaces of all of the classes, said sub-space (SED) being defined by the plurality of variables (VD) comprised in the sets (VDj) of synthetic variables of the plurality of classes: and that the input layer of the neural network comprises a plurality of neurones each corresponding to a respective variable (V) of the plurality of synthetic variables which define the discrimination sub-space (SED).

The present invention also provides a learning method of a classification apparatus comprising means for acquiring, by a plurality of channels, raw data representing instances of a plurality of different classes; a unit processing said raw data and a neural network comprising an input layer, an output layer and at least one intermediate layer disposed between the input and output layers, the output layer comprising a plurality of neurones each being adapted to recognise instances of a respective class from the plurality of classes, this apparatus being notably for use in the recognition or the characterisation of odours, the method comprising the steps of: applying to the raw data acquisition means, during a learning phase, a plurality of instances of the plurality of classes, the classes to which the instances belong being known; and processing said raw data, by the data processing unit, so as to determine for each class (j) characteristics common to the different instances of the class; characterised in that the processing step comprises the determination, by the data processing unit, for each class (j), of a sub-space (SEj) in which the instances of this class (j), for which raw data has been obtained, are optimally separated from the instances of all the other classes, said sub-space (SEj) being defined by a set (VDj) of one or a plurality of synthetic variables (V), and determining the discrimination sub-space (SED) which comprises the sub-spaces (SEj) of all the classes, said sub-space (SED) being defined by the plurality of variables (VD) comprised in the groups (VDj) of synthetic variables of the plurality of classes; and in that the neural network is provided with an input layer comprising a plurality of neurones for receiving, respectively, as input a value of a respective variable of the plurality of synthetic variables (VD) defining the discrimination sub-space (SED).

The apparatus and the method according to the present invention use the intertwining of the results of a statistical analysis and a neural network so as to draw maximum benefit from the advantages provided by each of these. More particularly, by choosing for input into the neural network the synthetic variables which best discriminate the different classes, there is a significant increase in the contribution in terms of qualitative information, which leads to a reduction in the duration of the learning phase and an increase in the speed of identification of samples during the identification phase.

The choice of synthetic variables which best discriminate the different classes can be made manually or using an automated search. A preferred automated search method consists in the determination, in each of a plurality of different sub-spaces corresponding to combinations of respective different variables, of a region encompassing the points representing the different instances of this class, and the determination of the sub-space in which the determined region both is the furthest from the regions representing the other classes and has the smallest possible size.

In a preferred embodiment of the invention, the neural network comprises, as intermediate layer, a plurality of individual neural networks each corresponding to a respective class of the plurality of classes. By using this structure of the neural network, it is possible to reduce the duration of the learning phase to a significant extent, which can be of extreme importance when classification of instances of a large number of classes is involved. The training of such a neural network involves the separate training of the individual neural networks.

In certain applications it can be useful, or necessary, to eliminate from the analysis raw data corresponding to channels which do not contribute to the differentiation of instances of different classes. It can also be necessary to eliminate from the calculations the data concerning abnormal instances of a class, that is, the instances which, in terms of synthetic variables, are far away from other instances of the same class. This improves the reliability of the identification model established during the learning phase.

Preferably, the neural networks of the invention are supervised networks the neurones of which apply sigmoid functions. Preferably, the neural networks according to the invention are trained using the back propagation algorithm.

The raw data processing unit applies statistical processing such as a principal component analysis, a discriminant factor analysis, or other similar methods.

So as to check the reliability of the identification model established during the learning phase of the apparatus, it is preferable to determine the sub-spaces (SEj), the sets of synthetic variables and the discrimination sub-space (SED) based on raw data relating to only a certain percentage of the data acquired during the learning phase. The other data is applied to the processing unit so as to calculate values corresponding to the synthetic variables, these values being applied to the neural network and the classifications performed by the neural network being compared with the true classes to which the instances involved belong. If the class identification rate exceeds a threshold value, for example, 80%, then the training of the apparatus is ended and the apparatus can be used for identifying instances of unknown class.

BRIEF DESCRIPTION OF THE DRAWINGS

Particular embodiments of the invention will now be described, as non-limiting examples, in association with the annexed drawings, in which:

FIG. 1 is a flow diagram illustrating the different steps of the statistical pre-processing which is applied in the first preferred embodiment of the invention;

FIGS. 2A and 2B are graphs showing the distribution of data obtained by a principal component analysis and representing instances of five different classes in a plane enabling the different classes to be distinguished from one another, in which;

FIG. 2A shows the distribution of the points, and

FIG. 2B shows the boundaries defined to delimit the regions corresponding to the different classes;

FIG. 3 is a diagram indicating the overall structure of a conventional neural network;

FIG. 4 is a diagram illustrating the main steps in the design of a complete network according to the first preferred embodiment of the invention;

FIG. 5 is a graph illustrating the case of a sub-space in which two classes from six classes of products are well distinguished from the others; and FIG. 6 schematically shows the structure of a neural network according to the second embodiment of the invention.

DETAILED DESCRIPTION OF THE PREFERRED EMBODIMENTS

Preferred embodiments of the apparatus according to the invention will now be described in the context of odour recognition apparatus. However, it is to be understood that the present invention is not limited to such applications but is equally well applicable in other fields where data representing instances of different classes must be classified.

A first embodiment of the invention will now be described with reference to FIGS. 1 to 4. This embodiment uses apparatus of the so-called <<electronic nose>> type, comprising p sensors. These sensors can include sensors of conventional types, such as, for example, conductive polymer sensors, quartz piezoelectric sensors; semiconductive oxide sensors, etc. During the learning phase of the apparatus, several samples of known products are presented to the apparatus so as to generate raw data (a learning database) which will then be analysed to establish an identification model. The analysis consists in performing certain statistical pre-processing steps, the allocation to each class of synthetic variables enabling the best discrimination of instances of this class from the instances of the other classes, and the establishment of the structure of a neural network on the basis of the results of these processes. FIG. 1 summarises the different steps of this analysis.

STATISTICAL PREPROCESSING STEPS

The establishment of a learning database

Several selected sensors are used in an "electronic nose". To each analysed sample i, there is associated a point $\chi_i$ in a p-dimensional space, p being the number of sensors.

$$\chi_i = \sum_{k=1}^{p} x(i,k) e_k \text{ where } k = 1 \text{ to } p$$

$e_k$ is a p-dimensional vector whose components are all equal to 0 except for the $k^{th}$ which is equal to 1. The group of these vectors forms a basis of the space. $x(i,k)$ is the measurement given by the $k^{th}$ sensor during analysis of i. The set of these representations forms a "cloud" or distribution of points.

Generally, during the learning phase of this apparatus, several samples are analysed. Depending upon the applications, these samples can be derived from different products (PCJ/j=1 to n) or from the same product in different states (good, bad, borderline) or at different concentrations. At the end of the first stage of the learning phase (the "data acquisition" phase), there is obtained a data table or matrix X of dimensions (m,p), m being the total number of analysed samples (that is i takes the values 1 to m).

The goal then aimed at is to determine if the apparatus enables different products to be differentiated, the samples of a same product to be identified.

A metric M is defined over the space containing the points. Certain statistical elements are also defined over the centred table X, in particular, the covariance matrices V, the interclass B and intraclass W variances, and the centres of gravity ($g_j/j=\{1;n\}$, n being the number of analysed products) of the classes defined by the samples of the different products (see, for example, G. Saporta "Probabilites, Analyse des donnees et Statistique", Editions TECHNIP (1990), for the calculation of these items).

Choice of Sensors

During the statistical pre-processing, the sensors which best discriminate the different products are chosen automatically. This choice is based on a step-by-step search for the best combination. M. C. Constanza and A. A. Afifi have proposed an appropriate alogorithm (in the Journal of the American Statistical Association, Vol.74, Number 368 (1979)). The non-selected sensors will not be taken into account in any of the analyses.

Determination of the Synthetic Variables

Synthetic variables can be allocated to each product by using several types of statistical analysis, for example, PCA or DFA.

PCA enables the selected sensors to be replaced by new, non correlated synthetic variables (Cj, j=$\{1;p\}$) which explain the maximum of quantitative information contained in the data table. In PCA, a particular basis (cj,j=$\{1;p\}$) of the space is sought. The synthetic variable Cj is, then, associated with the vector cj.

The vectors (cj,j=$\{1;p\}$) are the orthonormal eigenvectors M of the matrix VM. See, for example, Gene H. Golub & Charles F. Van Loan "Matrix Computations", The Johns Hopkins University Press (1990) for the calculation of the proper elements. The synthetic variables are then defined by:

$$Cj(x)=x'M\ cj$$

where j=$\{1;p\}$, x' being the transpose of x. Generally, M is associated with the identity matrix.

For its part, DFA enables the selected sensors to be replaced by new synthetic variables (Uj,j=$\{1;p\}$) which best discriminate the different products. In DFA, a particular basis (uj,j=$\{1;p\}$) of the space is sought. The synthetic variable Uj is then associated with the vector uj.

The vectors (uj, j=$\{1;p\}$) are the orthonormal eigenvectors $W^1$ of the matrix $BW^1$. See supra Gene H. Golub & Charles Van Loan <<Matrix Computations>> for the calculation of the eigen elements. The synthetic variables are then defined by:

$$Uj(x)=x'W^{-1}uj$$

where j=$\{1;p\}$, x' is the transpose of x and $W^{-1}$ is the inverse of the matrix W.

Allocation of Synthetic Variable to Each Class

The exploration of the different sub-spaces generated by the new synthetic variables V (whether they are determined by PCA, DFA or by another method) enables the discrimination of each of the products. This exploration or searching can be performed manually by visualising the different planes, or in an automatic fashion by searching for the best combination of these variables. This method makes it possible to associate to each product PCj the set VDj of the synthetic variables V which best discriminates it from the other products. This set VDj of variables generates a $p_j$-dimensional sub-space SEj in which a specific region Rj is associated with it. This region must not overlap that of another product, or the region of overlap must be as small as possible. The sub-space SEj is described by a number of synthetic variables fewer than p. The set of all of these synthetic variables forms the discrimination sub-space referenced SED.

$$SED = \bigcup_{j=1}^{n} SEj$$

FIG. 2A illustrates an example of the results of a typical analysis and represents the projection of the samples of five products onto a plane defined by two synthetic variables obtained by a PCA and identified by an exploration of the different possibilities. It will be seen that the different products are well differentiated. In this case, all of the sub-spaces SEj and SED are constituted by a single plane, that is, for all of the classes j the synthetic variables VDj which enable them to be best discriminated are the same ($VD_1=VD_2=VD_3=VD_4=VD_5$).

The search for VDj can be performed visually, by displaying graphical representations of the measurement points in sub-spaces of two or three dimensions (corresponding to combinations of two or three variables V). This search can also be performed automatically following, for example, the method described below.

The reference CV is used to designate the set of all the possible combinations of synthetic variables. For each element CV(k) of CV, the set of points corresponding to the raw data is projected onto the sub-space SEk defined by the variables of the combination CV(k) concerned. In the projection space, the convex envelopes of each class are calculated. These convex envelopes delimit regions Rj corresponding to each product (class), as shown in FIG. 2B for the example of FIG. 2A. Several algorithms enable this envelope to be defined. In particular, B. Chazelle (in <<Discrete Computational Geometry>>, 10, pp.377–409 (1993)) proposed an algorithm for the multidimensional case.

If the surface area or the volume of the region Rj delimited by the envelope associated with the class j in the sub-space SEk is designated CV(k,j), and the surface area or the volume separating two classes j' and j in this sub-space SEk is designated CV(k,j'j) (whose value is 0 in the case where classes j and j' overlap), it is preferable to associate to class j a class kj which minimises CV(k,j) and for which CV(k,j'j) is maximised. VDj will then be the combination of variables $$\frac{CV(k, kj, j)}{CVi(k, j)}$$

is maximised. In other words, VDj defines the sub-space SEj in which the class j is best separated from all the other classes.

In the case where for each k, CV(k,kj,j),=0, that is the class j overlaps with the class kj in all of the possible sub-spaces, then the following criterion can be used: choose the combination of variables VDj for which $$\frac{CV(k, j)}{CV(k, kj, j)}$$

is maximised, where CVi(k,j',j) is a measure of the intersection of the two classes j and j'.

The statistical methods also enable detection of abnormal points. A sample of a product PCj will be identified as abnormal if, when this point is eliminated, the variation in the volume or surface area of the region Rj is greater than a certain percentage (for example 10%).

The detected abnormal points are eliminated from the database. The deletion of these points enables the database to be filtered. The employed statistical method is then reapplied to the filtered database.

In the above-described embodiments, the choice of the variables VDj is performed by seeking to best discriminate each class from the others. However, the case can be envisaged where two combinations $VDj^A$, $VDj^B$ enable a class j to be discriminated from the others, and that the combination $VDj^A$ which enables best discrimination of this class from all the others uses one or a plurality of variables V which are useful only with respect to discrimination of this class j. In such a case, so as to minimise the total number of variables necessary to discriminate the different classes from each other (and to reduce the dimensions of the discrimination sub-space SED) it can be decided to associate class j with the combination of variables $VDj^B$.

It is appropriate to note that, in certain applications, one or a plurality (or all) of the synthetic variables which best discriminate the different classes, can be constituted, respectively, by one or a plurality of the initial variables, that is, the output signals from one of the sensors. More particularly, a synthetic variable V (which will here be called $Y^k$) can be constituted by a linear combination of the initial variables X and, thus, designating the set of initial variables $X^j$, where j=1 to p, $$Y^k = \sum_{j=1}^{p} \alpha_{kj} X^j$$

(the coefficients ($\alpha_{kj}$ are real numbers). A synthetic variable of this type can thus be associated with a variable $X^k$ of a sub-set of the initial variables which best discriminate a class from the others, where $$X^k = \sum_{j=1}^{p} \alpha_{kj} X^j$$

Now, in certain cases the process of optimising the discrimination criteria (such as those described above) will result in a determination that, for one or a plurality of the synthetic variables of this type, all of the coefficients $\alpha_{kj}$ are equal to zero except for $\alpha_{kk}$ which will be equal to 1.

NEURAL NETWORK CONSTRUCTION

Some information about neural networks in general

A neural network is defined by its architecture, the learning rule which alters the weights of the links between neurones, and the information transfer functions from one layer to another. The architecture includes the number of layers, the number of neurones in each layer and the links between the neurones of different layers. The number of neurones in the first layer is the dimension of the space. The network is called <<supervised>> if the desired output from each neurone of the hidden layer is known (see, for example, J. Hérault & C. Juten, "Reseaux neuronaux et traitement de signal", HERMES (1993)).

FIG. 3 shows a simple three-layer network.

In the case of the invention, the most appropriate neural networks are supervised networks. The number of neurones in the input layer is the number of variables (sensors) describing the samples and that of the output layer is the number of classes (products).

The transfer functions towards the output neurones are sigmoid functions of such a kind that the value attributed to each of these neurones is between 0 and 1.

In general, the union VD of the sets VDj of synthetic variables enables a better separation of the different products. Consequently, it is preferable to use them for constructing the neural networks. In fact, among the initial variables some are redundant and others are affected by noise. This is not the case with the synthetic variables.

In the first preferred embodiment of the invention, these variables are used to construct a complete neural network of a new type.

Complete Neural Network

In this network, the number of neurones in the input layer is equal to the dimension of the sub-space SED. Each neurone is associated with one of the synthetic variables of the set VD. The signal input to this neurone is the value taken by this variable in the input vector. The number of neurones in the output layer is equal to the number of products.

The number of hidden layers, as well as the number of neurones in each of these, can be variable.

The diagram of FIG. 4 shows the process for constructing this network.

This approach enables a more rapid convergence than the conventional approach, since the variables that are used are more discriminating and their number is lower than that of the sensors. In the majority of applications implemented so far, this number is lower than five.

Once the neural network has been set up, the classification apparatus can be used to identify samples of unknown products, optionally after a validation of the identification model inherent in the developed neural network. Such a validation can be performed by using, for the setting up of the neural network, the results of statistical pre-processing performed on the database relating to only a certain percentage (for example 50%) of the samples tested during the learning phase, and by verifying if the apparatus succeeds in correctly classifying the data obtained for the other samples.

The second preferred embodiment of the invention will now be described with reference to FIGS. 5 and 6. The second embodiment can use an apparatus of so-called <<electronic nose>> type identical to that used in the first embodiment. Further, in the second embodiment, during the learning phase, raw data is acquired and subjected to the same statistical pre-processing as in the first embodiment. However, in the second embodiment of the invention, the results of the statistical pre-processing are used to establish the structure of a neural network whose intermediate layer comprises a plurality of individual neural networks. Each of these individual neural networks is associated with a product. For each product, PCj, only the elements of VDj are taken into account. The combinational neural network possessing this structure enables a significant reduction to be achieved in the time necessary for the learning phase. This is particularly advantageous when the number of products to be analysed is great.

Individual Network

In the pre-processing phase, a sub-space SEj is associated with the product PCj. This sub-space can be the same for more than one product. In SEj, the cloud of points is structured into several regions, one of which is associated with the product PCj. Each of the other regions is associated with one or several products. This case arises when certain of the components of certain products are the same. FIG. 5 illustrates this case. The products PC1 and PC2 are well separated from all the others. This plane is thus the sub-space SE1 and SE2.

A network is constructed to identify the products PCj with which a sub-space SEj is associated. The number of neurones pj of the input layer is equal to the dimension of the sub-space SEDj. Each neurone is associated with one of the synthetic variables of the set VDj. The number of neurones of the output layer is equal to the number of regions that are well discriminated in SEj. A certain number of products is thus identified by this network.

The number of hidden layers as well as the respective numbers of neurones therein can be variable.

The number of individual networks is less than the number of analysed products.

Combinational Network

This network is made up of the combination of all the individual networks. The first layer of this network is the same as that of the global network described above with regard to the first embodiment of the invention. The second layer is formed of the set of individual networks described above. The number of neurones of the output layer is equal to the number of analysed products. Each neurone represents a product. It is connected, at most, to one output neurone of each individual network. The signal output by each of these neurones is the maximum of the inputs thereof.

In order to train the network, the different individual networks are trained separately.

The diagram of FIG. 6 illustrates the architecture of such a network.

Modifications can be made in the above-described embodiments without departing from the scope of the present invention. For example, in the context of the application of the present invention in an apparatus of so-called <<electronic nose>> type, in the statistical pre-processing, the data from the sensors can be associated with other measurements from one or more detectors of environmental parameters (such as a temperature sensor or a humidity sensor). These latter measurements can play a particular role by defining, for example, appropriate metrics. On the other hand, in most cases, the variables VDj involve a linear discrimination of the product PCj from the other products. Thus, instead of building a combinatory network comprising individual non-linear networks, individual linear networks can be used. In each of these networks, hyperplanes are sought which best separate one or more products PCj. An example of these hyperplanes is illustrated in FIG. 6, where the hyperplanes are indicated by dotted lines.

Although preferred embodiments of the invention have been described hereabove, it should be recalled that the present invention is not limited to these embodiments, which are described as non-limiting examples.

What is claimed is:

1. Classification apparatus, notably for use in the recognition or the characterisation of odours, comprising:

means for acquiring, by a plurality of channels during a learning phase, raw data representing a plurality of instances of a plurality of different classes;

a processing unit for processing said raw data so as to determine, for each class (j), characteristics common to the different instances of this class; and a neural network for outputting a classification, into one of the classes, of an instance presented to said classification apparatus, said neural network comprising an input layer, an output layer and at least one intermediate layer disposed between the input and output layers, the output layer comprising a plurality of neurones each being adapted to recognise instances of a respective class from the plurality of classes;

characterised in that the processing unit determines for each class (j) a sub-space (SEj) in which the instances of this class (j), for which raw data has been obtained, are optimally separated from the instances of all the other classes, said sub-space (SEj) being defined by a set (VDj) of one or a plurality of synthetic variables (V), and determining the discrimination sub-space (SED) which comprises the sub-spaces of all of the classes, said sub-space (SED) being defined by the plurality of variables (VD) comprised in the sets (VDj) of synthetic variables of the plurality of classes;

and in that the input layer of the neural network comprises a plurality of neurones each corresponding to a respective variable (V) of the plurality of synthetic variables (VD) which define the discrimination sub-space (SED).

2. Classification apparatus according to claim 1, characterised in that the processing unit selects for each class (j) the sub-space (SEj) in which the cluster of instances of this class (j) is the farthest from the clusters of instances of the other classes and the spread of the cluster of the class (j) is minimised.

3. Classification apparatus according to claim 1, characterised in that, in a case where in all the possible sub-spaces at least one cluster of the instances of a class overlaps with a cluster of the instances of another class, the processing unit selects for each class (j) the sub-space (SEj) in which the ratio of the spread of the cluster of instances of this class (j) to the degree of overlap is maximised.

4. Classification apparatus according to claim 1, characterised in that the processing unit selects the sub-space (SEj) to associate with a class (j) by determining, in each of a plurality of different sub-spaces, the convex envelope of the region (Rj) which contains the points corresponding to the instances of said class (j) and by determining the sub-space in which this region (Rj) is best separated from the regions corresponding to the other classes.

5. Classification apparatus according to claim 4, characterised in that the processing unit identifies instances of a class as being abnormal if the change in the dimensions of the region (Rj) necessary to encompass the point corresponding to this instance represents an increase greater than a certain percentage of the dimensions of the region (Rj) that encircles the other points relating to this class.

6. Classification apparatus according to claim 1, characterised in that the raw data processing unit is adapted to identify the channels whose data does not help to differentiate instances of different classes, and to determine the sub-spaces (SEj), the sets (VDj) of synthetic variables and the discrimination sub-space (SED) based on data excluding the data from the thus-identified channel(s).

7. Classification apparatus according to claim 1, characterised in that the neural network is a supervised network the neurones of which apply sigmoid functions and which is trained using the back propagation algorithm.

8. Classification apparatus according to claim 1, characterised in that the intermediate layer, or layers, of the neural network comprise a plurality of individual neural networks, one for each of the plurality of classes, the neurones of the input layer of each individual network being connected to the neurone, or neurones, of the input layer of the global network which corresponds to the synthetic variables of the set (VDj) which defines the sub-space (SEj) in which the instances of this class are differentiated from the instances of the other classes.

9. Classification apparatus according to claim 8, characterised in that the training of the complete neural network comprises the separate training of the individual neural networks.

10. Classification apparatus according to claim 1, characterised in that the data processing unit determines the sub-spaces (SEj), the sets (VDj) of synthetic variables and the discrimination sub-space (SED) based only on raw data relating to a certain percentage of the instances for which data has been acquired during the learning phase, the raw data relating to the other instances being used to perform a validation of the classification effectiveness of the neural network.

11. Classification apparatus according to claims 1, characterised in that the data processing unit applies a principal component analysis or a discriminant factor analysis to determine the synthetic variables.

12. A learning method of a classification apparatus comprising means for acquiring, by a plurality of channels, raw data representing instances of a plurality of different classes, a unit processing said raw data and a neural network comprising an input layer, an output layer and at least one intermediate layer disposed between the input and output layers, the output layer comprising a plurality of neurones each being adapted to recognise instances of a respective class from the plurality of classes, this apparatus being notably for use in the recognition or characterisation of odours, the method comprising the steps of:

applying to the raw data acquisition means, during a learning phase, a plurality of instances of the plurality of classes, the classes to which the instances belong being known; and processing said raw data, by the data processing unit, so as to determine for each class (j) characteristics common to the different instances of the class;

characterised in that the processing step consists in processing said raw data, by the data processing unit, so as to determine, for each class (j), a sub-space (SEj) in which the instances of this class (j), for which raw data has been obtained, are optimally separated from the instances of all the other classes, said sub-space (SEj) being defined by a set (VDj) of one or a plurality of synthetic variables (V), and in determining the discrimination sub-space (SED) which comprises the sub-spaces (SEj) of all the classes, said sub-space (SED) being defined by the plurality of variables (VD) comprised in the sets (VDj) of synthetic variables of the plurality of classes;

and in that the method further comprises the step of providing the neural network with a layer comprising a plurality of neurones for receiving, respectively, as input a value of a respective variable of the plurality of synthetic variables (VD) defining the discrimination sub-space (SED).

13. Classification apparatus according to claim 2, characterised in that the processing unit selects the sub-space (SEj) to associate with a class (j) by determining, in each of a plurality of different sub-spaces, the convex envelope of the region (Rj) which contains the points corresponding to the instances of said class (j) and by determining the sub-space in which this region (Rj) is best separated from the regions corresponding to the other classes.

14. Classification apparatus according to claim 3, characterised in that the processing unit selects the sub-space (SEj) to associate with a class (i) by determining, in each of a plurality of different sub-spaces, the convex envelope of the region (Rj) which contains the points corresponding to the instances of said class (j) and by determining the sub-space in which this region (Rj) is best separated from the regions corresponding to the other classes.

15. Classification apparatus according to claim 13, characterised in that:

the processing unit identifies instances of a class as being abnormal if the change in the dimensions of the region (Rj) necessary to encompass the point corresponding to this instance represents and increase greater than a certain percentage of the dimensions of the region (Rj) that encircles the other points relating to this class;

the raw data processing unit is adapted to identify the channels whose data does not help to differentiate instances of different classes, and to determine the sub-spaces (SEj), the sets (VDj) of synthetic variables and the discrimination sub-space (SED) based on data excluding the data from the thus-identified channel(s);

the neural network is a supervised network the neurones of which apply sigmoid functions and which is trained using the back propagation algorithm; and the intermediate layer, or layers, of the neural network comprise a plurality of individual neural networks, one for each of the plurality of classes, the neurones of the input layer of each individual network being connected to the neurone, or neurones, of the input layer of the global network which corresponds to the synthetic variables of the set (VDj) which defines the sub-space (SEj) in which the instances of this class are differentiated from the instances of the other classes.

16. Classification apparatus according to claim 14, characterised in that:

the processing unit identifies instances of a class as being abnormal if the change in the dimensions of the region (Rj) necessary to encompass the point corresponding to this instance represents and increase greater than a certain percentage of the dimensions of the region (Rj) that encircles the other points relating to this class;

the raw data processing unit is adapted to identify the channels whose data does not help to differentiate instances of different classes, and to determine the sub-spaces (SEj), the sets (VDj) of synthetic variables and the discrimination sub-space (SED) based on data excluding the data from the thus-identified channel(s);

the neural network is a supervised network the neurones of which apply sigmoid functions and which is trained using the back propagation algorithm; and the intermediate layer, or layers, of the neural network comprise a plurality of individual neural networks, one for each of the plurality of classes, the neurones of the input layer of each individual network being connected to the neurone, or neurones, of the input layer of the global network which corresponds to the synthetic variables of the set (VDj) which defines the sub-space (SEj) in which the instances of this class are differentiated from the instances of the other classes.

17. Classification apparatus according to claim 15, characterised in that:

the training of the complete neural network comprises the separate training of the individual neural networks;

the data processing unit determines the sub-spaces (SEj), the sets (VDj) of synthetic variables and the discrimination sub-space (SED) based only on raw data relating to a certain percentage of the instances for which data has been acquired during the learning phase, the raw data relating to the other instances being used to perform a validation of the classification effectiveness of the neural network; and the data processing unit applies a principal component analysis or a discriminant factor analysis to determine the synthetic variables.

18. Classification apparatus according to claim 16, characterised in that:

the training of the complete neural network comprises the separate training of the individual neural networks;

the data processing unit determines the sub-spaces (SEj), the sets (VDj) of synthetic variables and the discrimination sub-space (SED) based only on raw data relating to a certain percentage of the instances for which data has been acquired during the learning phase, the raw data relating to the other instances being used to perform a validation of the classification effectiveness of the neural network; and the data processing unit applies a principal component analysis or a discriminant factor analysis to determine the synthetic variables.

* * * * *

UNITED STATES PATENT AND TRADEMARK OFFICE
CERTIFICATE OF CORRECTION

PATENT NO. : 6,496,813 B1
DATED : December 17, 2002
INVENTOR(S) : Saïd Labreche et al.

It is certified that error appears in the above-identified patent and that said Letters Patent is hereby corrected as shown below:

Column 5,
Line 7, "<<electronic nose>>" should read -- "electronic nose" --;

Column 6,
Line 27, "<<Matrix Computations>>" should read -- "Matrix Computations" --;

Column 7,
Lines 16-17, "<<Discrete Computational Geometry>>" should read -- "Discrete Computational Geometry" --;
Line 27, "variables" should read -- variables such that --;
Lines 29-30, " $\frac{CV(k,kj,j)}{CVi(k,j)}$ " should read -- $\frac{CV(k,kj,j)}{CV(k,j)}$ --;

Lines 41-43, " $\frac{CV(k,j)}{CV(k,kj,j)}$ " should read -- $\frac{CV(k,j)}{CV_i(k,kj,j)}$ --;

Column 8,
Line 38, "<<supervised>>" should read -- "supervised" --;

Column 9,
Line 23, "<<electronic nose>>" should read -- "electronic nose" --;

Column 10,
Line 13, "<<electronic nose>>" should read -- "electronic nose" --; and Column 12,
Line 41, "class ( i ) by" should read -- class ( j ) by --.

Signed and Sealed this

Twenty-fourth Day of August, 2004

JON W. DUDAS
*Director of the United States Patent and Trademark Office*